US006765072B1

(12) United States Patent
Willimann et al.

(10) Patent No.: US 6,765,072 B1
(45) Date of Patent: Jul. 20, 2004

(54) PROCESS FOR THE PREPARATION OF AQUEOUS DISPERSIONS OF LATEX PARTICLES HAVING A HETEROGENEOUS MORPHOLOGY, THE LATEX PARTICLES OBTAINABLE WITH THE PROCESS, THE DISPERSIONS AND REDISPERSIBLE POWDERS, AS WELL AS THE USE THEREOF

(75) Inventors: Hongli Willimann, Merenschwand (CH); Robert Koelliker, Oberkirch (CH)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/744,088

(22) PCT Filed: Jul. 21, 1999

(86) PCT No.: PCT/EP99/05205

§ 371 (c)(1),
(2), (4) Date: Mar. 21, 2001

(87) PCT Pub. No.: WO00/05276

PCT Pub. Date: Feb. 3, 2000

(30) Foreign Application Priority Data

Jul. 22, 1998 (DE) .......................................... 198 33 061

(51) Int. Cl.[7] .............................. C08F 2/24; C08F 2/28; C08F 291/00; C08L 101/12; C04B 24/26
(52) U.S. Cl. ........................... 526/75; 526/81; 526/201; 526/217; 526/317.1; 526/318.6; 526/347

(58) Field of Search .......................... 523/201; 524/458, 524/460, 556; 526/75, 81, 201, 217, 317.1, 318.6, 347

(56) References Cited

FOREIGN PATENT DOCUMENTS

| EP | 0 426 391 | 5/1991 | ......... C08F/265/04 |
| EP | 426391 A * | 5/1991 | ............. C08F/2/22 |
| EP | 0 696 602 | 2/1996 | ......... C08F/285/00 |
| EP | 696602 A1 * | 2/1996 | ......... C08F/285/00 |

* cited by examiner

Primary Examiner—Kelechi C. Egwim
(74) Attorney, Agent, or Firm—Thomas F. Roland; Charles W. Almer

(57) ABSTRACT

The invention relates to a process for the preparation of aqueous dispersions of latex particles having a heterogeneous morphology by a semicontinuous emulsion polymerization, comprising the emulsion polymerizing of ethylenically unsaturated (co)monomers, accompanied by, the addition of cationic and/or anionic and/or nonionic emulsifiers and/or protective colloids as stabilizers, which are directly used as such or synthesized in situ, the semicontinuous emulsion polymerization being performed in the presence of the stabilizer or stabilizers with a monomer mixture, which a) contains at least one nonionic, ethylenically unsaturated monomer with a glass transition temperature Tg above about 30° C. in a quantity of about 10 to 70 wt. %, based on the total weight of ethylenically unsaturated (co)monomers and b) at least one hydrophilic, ethylenically unsaturated monomer in a quantity of about 5 to 30 wt. %, based on the total weight of ethylenically unsaturated (co) monomers.

21 Claims, 2 Drawing Sheets

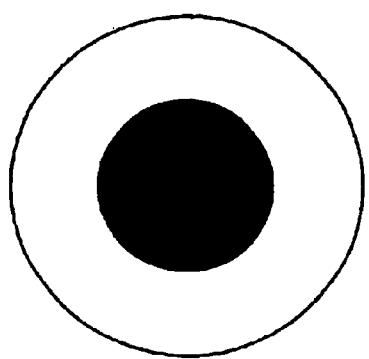
Fig. 1a
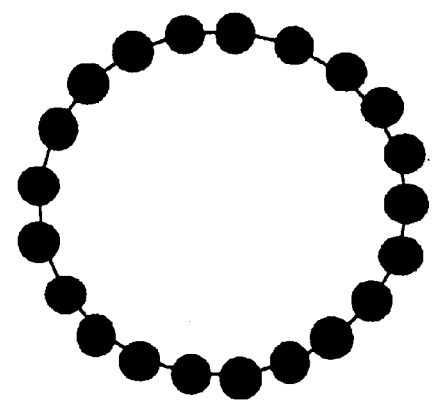
Fig. 1b
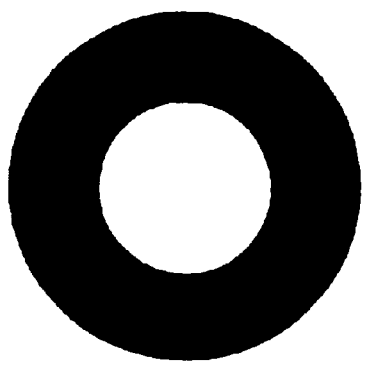
Fig. 1c
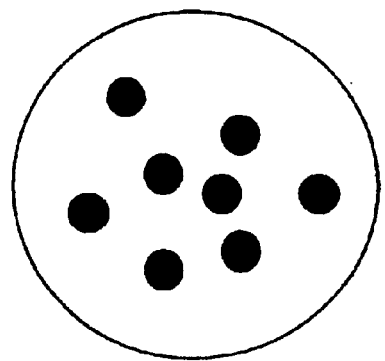
Fig. 1d
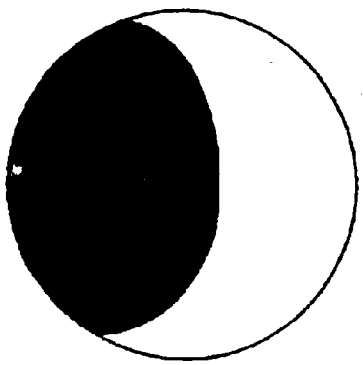
Fig. 1e
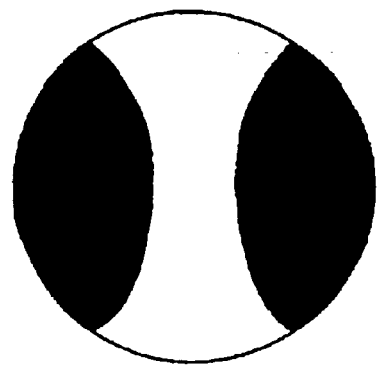
Fig. 1f
Fig. 1

PROCESS FOR THE PREPARATION OF AQUEOUS DISPERSIONS OF LATEX PARTICLES HAVING A HETEROGENEOUS MORPHOLOGY, THE LATEX PARTICLES OBTAINABLE WITH THE PROCESS, THE DISPERSIONS AND REDISPERSIBLE POWDERS, AS WELL AS THE USE THEREOF

FIELD OF THE INVENTION

The invention relates to a process for the preparation of aqueous dispersions of latex particles having a heterogeneous morphology. The invention also relates to the latex particles preparable with the process, the aqueous dispersions and redispersible powders, as well as the use thereof.

BACKGROUND OF THE INVENTION

Emulsion polymerization is a known procedure for the production of latex polymers having a clearly defined structure. In this connection particular interest is placed on a process leading to the production of so-called heterogeneous latex morphologies. As a result of their molecular structure, such latex particles provide special characteristics and a wide range of uses. In this heterogeneous structure of the latex particles, a distinction is made between a relatively hydrophobic and a relatively hydrophilic area. For thermodynamic equilibrium reasons, under normal conditions there is a hydrophilic shell (outer phase) and a hydrophobic core (inner phase), because these can be more easily produced in general by emulsion polymerization. However, it is much more difficult to produce systems with a so-called inverse core-shell structure, in which the core is hydrophilic and the shell hydrophobic. Increasing importance is being attached thereto as a result of the possible encapsulation of functionalized, hydrophilic polymers.

Such a structure of polymer particles with inverse core-shell structure and their production by emulsion polymerization are described by EP 426 391 A2. According to the process described therein 2 to 60 parts by weight in the form of the core polymer (A) are produced by the emulsion polymerization of 10 to 80 parts by weight of an acrylate ester with an alkyl group with 1 to 3 carbon atoms having 90 to 20 parts by weight of a further monomer. The shell polymer (B) is subsequently produced, e.g. by emulsion polymerization from 98 to 40 parts by weight of at least one vinyl monomer, after which the core polymer is hydrolyzed in alkaline manner. Preferably the shell polymer has a glass transition temperature of at least 50° C. Mention is also made of surfactants, which can optionally be used in a quantity of 0.1 to 10 wt. %. The particles are used as a pigment or filler in paints and paper coatings. An inadequate storage stability is a disadvantage of the dispersions described. In addition, the dispersed core-shell particles do not have a satisfactory resistance to water, so that after a certain time it is no longer possible to use them. The particle sizes which can be produced with the process of EP 426 391 A1 are also very ununiform and spread over a wide range, so that the uniform particle sizes necessary in certain applications are not available.

An encapsulation of hydrophilic polymers and the production thereof are also described in EP 696 602 A1. In the latter, the hydrophilic core is formed from 5 to 100 wt. % hydrophilic monomer and 0 to 95 wt. % nonionic monomer and the hydrophobic shell of 90 to 99.99 wt. % nonionic monomer and 0.1 to 10 wt. % acid-functionalized monomer. The acid-functionalized monomer is a carboxylic acid monomer, preference being given to (meth)acrylic acid. It is also possible to use non-polymerizable carboxylic acids, such as $C_6$–$C_{12}$ aliphatic or aromatic monocarboxylic or dicarboxylic acids. Styrene is mentioned as the preferred nonionic monomer for the shell. The particle size is preferably between 50 and 2000 nm. Additionally the core can contain less than 20, preferably 0.1 to 3 wt. % of multiply unsaturated monomers or 0.1 to 60 wt. % butadiene.

In the preparation process of EP 696 602 A1, the time sequence during the addition of the acid monomer in preparing the shell is of vital importance. If the core particle size is below 130 nm, the acid monomer must be added during the first 50% of the addition of the total shell monomer, preferably during the first 25% and in particularly preferred manner during the first 10%. If the core particle size exceeds 130 nm, the acid monomer must be added during the 100% addition of the total, added shell monomer, preferably during the first 50%, in particularly preferred manner during the first 25% and more especially during the first 10%. The core polymer can also be prepared by means of a seed, the average particle size being about 30 to 200 nm. Optionally both anionic and nonionic emulsifiers can be used, it being possible to use 0 to 0.75 wt. % emulsifier, based on the total core polymer, for the preparation of the core. It is unnecessary to add additional emulsifier during the preparation of the shell, but mention is made of tile addition of 0.05 to 2 wt. %, based on the total shell polymer weight. By adding bases the acid functions of the core can be neutralized and then the core swells, the polymers diffuse out of the core and particles with voids are formed. The latex particles prepared with the voids produced are more particularly used in aqueous coating compositions, such as water-based paints and paper coatings and give the latter brightness and body. A disadvantage of this process is the timing which must be carefully respected during the addition of the acid polymer for polymerizing the shell polymer, as well as the dependence of the alternative procedure on the core polymer particle size. The polymerization process is also very complex and technically complicated as a result of the described alternatives. The emulsifiers are only optionally used, mention only being made of anionic and nonionic emulsifiers.

The problem of the invention is to so further develop the aqueous dispersions or latex particles prepared according to the aforementioned processes, that whilst maintaining advantageous characteristics or in individual cases providing improved characteristics, the process control and the selection of the starting materials can be made more flexible, whilst simultaneously providing a simplified production procedure. In addition, the preparable latex particles, both in dispersed form and in powder form, must have a good storage stability and water resistance. In addition, these dispersions or the dispersed latex particles must be improved in such a way that during their final applications, such as e.g. in plastics-containing, cement-bound systems, as a result of desirable consecutive reactions, they lead to advantageous use products with improved processability and characteristics.

SUMMARY OF THE INVENTION

According to the invention, the above problem is solved by a process for the preparation of aqueous dispersions of latex particles having a heterogeneous morphology by a semicontinuous emulsion polymerization, comprising the emulsion polymerizing of ethylenically unsaturated (co) monomers, accompanied by the addition of cationic and/or anionic and/or nonionic emulsifiers and/or protective colloids as stabilizers, which are directly used as such or synthesized in situ, the semicontinuous emulsion polymerization being performed in the presence of the stabilizer or stabilizers with a monomer mixture, which a) contains at least one nonionic, ethylenically unsaturated monomer with a glass transition temperature Tg above about 30° C. in a quantity of about 10 to 70 wt. %, based on the total weight of ethylenically unsaturated (co)monomers and b) at least one hydrophilic, ethylenically unsaturated monomer in a quantity of about 5 to 30 wt. %, based on the total weight of ethylenically unsaturated (co)monomers.

BRIEF DESCRIPTION OF DRAWINGS

FIG. 1a) is a core-shell structure.

FIG. 1b) is a raspberry structure.

FIG. 1c) is an inverse core-shell structure.

FIG. 1d) is a domain structure.

FIG. 1e) is a half-moon structure.

FIG. 1f) is a sandwich structure.

DESCRIPTION OF THE INVENTION

Figure 2:
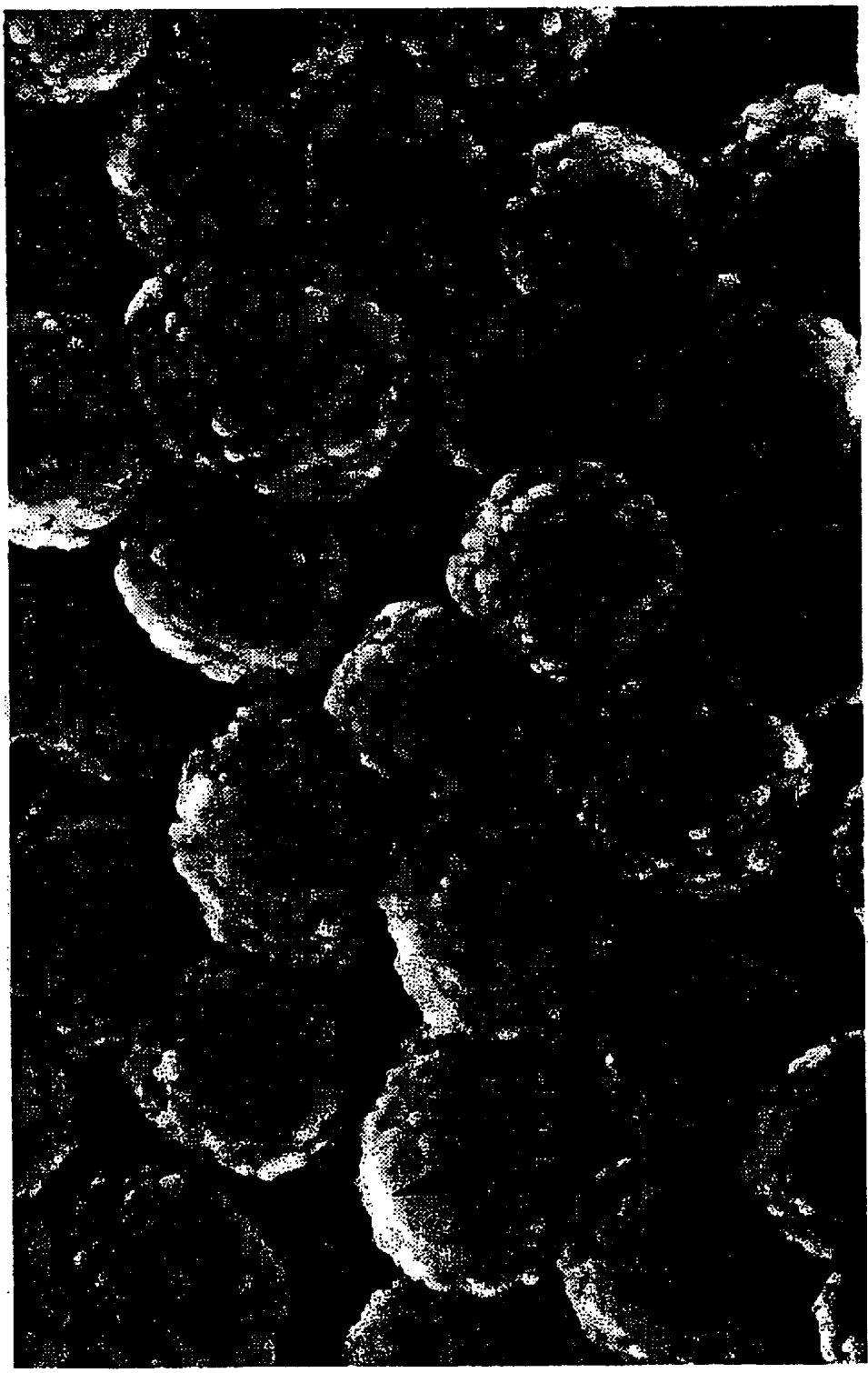
FIG. 2 is a photograph of an inventive particle of about 70 nm diameter that shows the raspberry-like structure.

The process according to the invention permits a simplified preparation of latex particles with heterogeneous morphology by a semicontinuous emulsion polymerization. Within the scope of the invention, there is no limitation with respect to the choice of the ethylenically unsaturated (co)monomers. It is possible to use any random (co)monomers, including said hydrophilic or nonionic (co)monomers.

The emulsion polymerization of the ethylenically unsaturated (co)monomers is performed accompanied by the addition of cationic and/or anionic and/or nonionic emulsifiers and/or protective colloids as stabilizers. Preferably the stabilizer or stabilizers are used in a quantity of about 1.0 to 20 wt. %, based on the total weight of the ethylenically unsaturated (co)monomers. The stabilizers in the form of emulsifiers and/or protective colloids selected within the scope of the invention are not subject to any restriction. Emulsifiers usable according to the invention can be nonionic emulsifiers, such as e.g. alkyl phenol EO (degree of ethoxylation) 10 or EO 50, particularly nonyl phenyl EO 10 or EO 50, alkyl alcohol EO 15 or EO 25, particularly $C_{13}$ alcohol EO 15 or EO 25, sorbitan fatty acid esters, ethoxylated fatty acid esters, glycerol fatty acid esters, ethoxylated alkyl amine; anionic emulsifiers such as ammonium, sodium or calcium salts of different fatty acids, alkyl aryl sulphonic acids, alkyl sulphonates, alkyl ether sulphates, alkyl sulphate esters, ethoxylated alkyl ether sulphonates, ethoxylated alkyl allyl ether sulphonic acid esters, alkyl phenol ether sulphates, dialkyl sulphosuccinates and also cationic emulsifiers, such as in particular alkyl ammonium acetate, quaternary ammonium group-containing compounds and pyridinium compounds.

As protective colloids can e.g. be used polyethylene oxide, starch and starch derivatives, gelatine, casein and other water-soluble proteins, water-soluble cellulose derivatives, such as hydroxyethyl cellulose, polysaccharides, water-soluble polyacrylates, such as acrylic acid copolymers, ethylene oxide-propylene oxide copolymers, polyvinyl alcohol and/or polyvinyl pyrrolidone and functionalized polyvinyl alcohols, such as acetoacetalised polyvinyl alcohol. Suitable protective colloids appear in Houben-Weyl, Methoden der organischen Chemie, vol. XIV/1, Makromolekulare Stoffe, Georg Thieme Verlag, Stuttgart, 1961, p 411–420.

It is surprisingly possible with a (co)polymer with cationic functionality as the stabilizer to achieve a stabilization of the dispersed particles corresponding to the action of the emulsifier or protective colloid. A dispersion-stable latex particle is produced by a type of "polymerizing in" of the (co)polymer with cationic functionality. The expression "(co)polymer with cationic functionality" is not particularly restricted, provided that it is obtained by (co)polymerization in aqueous medium of ethylenically unsaturated (co)monomers and there is at least one cationic function in the molecule. The term "polymer" covers homopolymers, block polymers or graft copolymers, as well as oligomers. It is obvious to the expert that any (co)polymerizable starting monomers with ethylenically unsaturated functionalities can be used for this polymer. Preferably, in the (co)polymer with cationic functionality, for about 1 part by weight monomer with cationic functionality there are 0 to 50, particularly about 0.1 to 20 parts by weight of (co)monomer.

The (co)polymer with cationic functionality results from copolymerizable, ethylenically unsaturated compounds. These are e.g. a vinyl ester with ($C_1$–$C_{18}$) carboxylic acids, e.g. vinyl acetate, vinyl propionate, etc.; a (meth)acrylate of ($C_1$–$C_8$) alcohols, e.g. methyl methacrylate, butyl methacrylate, octyl methacrylate, ethyl acrylate, isobutyl acrylate, 2-ethyl hexyl acrylate; a vinyl aromatic, such as e.g. styrene, vinyl toluene, vinyl chloride, an ethylene, an acrylonitrile, a diester of maleic acid and/or fumaric acid, a vinyl pyrrolidone, an amino acrylate or methacrylate ester, a vinyl pyridine, an alkylamino group-containing vinyl ether, an alkylamino group-containing acrylamide-methacrylamide or a quaternary ammonium group containing monomer, such as 2-hydroxy-3-acrylopropyl dimethyl ammonium chloride or 3-methacryloxypropyl dimethyl ammonium chloride or the like. Preferably the cationic functionality is attributed to a quaternary ammonium group. Preferably acrylates and/or methacrylates, as well as esters and amide compounds are used. The chain length between the ester/amide and the quaternary nitrogen is typically $C_2$ to $C_4$. It is also possible to use tertiary amines, which are protonated in the acid pH-range. Particularly preferred monomers for the preparation of the polymer with cationic functionality according to the invention are e.g. N,N-[(3-chloro-2-hydroxypropyl)-3-dimethyl ammonium propyl] methacrylamide chloride (DMAPMA-epi), N-[3-dimethylamino)-propyl]-methacrylamide hydrochloride (DMAPMA-HCl), N-[3-(trimethyl ammonium)-propyl]-methacrylamide chloride (MAPTAC), 2-hydroxy-3-methacryloxypropyl-trimethyl ammonium chloride, dimethyldiallyl ammonium chloride, aziridinyl ethyl methacrylate, morpholinoethyl methacrylate, trimethyl ammonium methyl methacrylate chloride, dimethylaminopropyl methacrylate, 1,2,2,6,6-pentamethyl piperidinyl methacrylate, aminopropyl vinyl ether, diethylaminopropyl ether and tert-butylaminoethyl methacrylate.

According to the invention, said stabilizers can be directly used as such or synthesized in situ and directly further processed. For example, the (co)polymer with cationic functionality can be prepared either in a preceding stage by homo or (co)polymerization of monomers with cationic functionality or with further comonomers and immediately, without isolation, further processed (in situ further processing). The (co)polymer with cationic functionality can also be initially prepared separately and isolated prior to further processing. It is obviously possible to use any commercially available emulsifier, any protective colloid or any (co)polymer with cationic functionality, which fulfils the aforementioned requirements.

If as the stabilizer according to the invention use is made of a (co)polymer with cationic functionality, then preferably in the (co)polymerizate obtained, for about 1 part by weight monomer with cationic functionality of the polymer (with cationic functionality), there are about 2 to 250, particularly about 10 to 150 parts by weight of remaining (co)monomers. According to the invention, the (co)polymerizate prepared contains about 0.001 to 50 mole %, particularly about 0.1 to 35 mole % monomer units with cationic functionality.

Preferably, besides cationic monomers, it is also possible to copolymerize monomers, whose protonated, reactive group or groups are deprotonated, accompanied by a corresponding rise in the pH-value. Such groups are known to the expert. Besides a cationic functionality, there can additionally be at least one anionic functionality in the (co) monomers. This leads to amphoteric systems, which are stable as such and do not coagulate. These surprising characteristics are not known in this form in the prior art.

According to a preferred embodiment, the emulsion polymerization is performed in the presence of in situ formed seed. For this purpose it is either possible to carry out a seed polymerization, accompanied by the addition of the stabilizer, or the actual stabilizer, such as e.g. the (co) polymer with cationic functionality, can be formed on the basis of a seed polymerization. For the formation of the seed during seed polymerization use is made of ethylenically unsaturated (co)monomers in a quantity of about 0.01 to 25 wt. %, based on the total weight of the ethylenically unsaturated monomers. In a seed polymerization, which is particularly suitable for producing monodisperse lattices, beforehand is provided a latex with a uniform particle size. The monomers to be polymerized are dosed into said seed latex in the monomer feed procedure. Polymerization is performed in such a way that the previously provided latex particles increase in volume, but do not quantitatively increase, whilst maintaining the monodispersity of the system. The number of particles is proportional to the previously provided fraction and a narrow particle size distribution is obtained.

The semicontinuous emulsion polymerization according to the invention is performed in the presence of the aforementioned stabilizer or stabilizers with a monomer mixture, the latter containing at least one nonionic, ethylenically unsaturated (co)monomer with a glass transition temperature Tg above 30° C. in a quantity of about 10 to 70 wt. %, based on the total weight of ethylenically unsaturated (co) monomers, and at least one hydrophilic, ethylenically unsaturated (co)monomer in a quantity of about 5 to 30 wt. %, based on the total weight of the ethylenically unsaturated (co)monomers.

It is important for the solution of the set problem, that the above-indicated parameters are respected. In particular, the glass transition temperature of the nonionic monomer must be above about 30° C. Preferably, the glass transition temperature of the nonionic monomer is between about 30 and 120° C., and in particularly preferred manner between about 50 and 110° C. This permits the setting of a high glass transition temperature of the polymer in the outer phase (shell), which contributes to the obtaining of a homogeneous distribution of the reactive groups present in the encapsulated, inner phase (core). On exceeding this Tg value, it is no longer possible to ensure a homogeneous distribution, particularly in the case of a large number of reactive groups.

The setting of the glass transition temperature Tg takes place in known manner by the choice and quantity of the monomers used. The weight fractions of the possible comonomers are chosen in such a way that the glass transition temperature Tg (midpoint temperature according to ASTM D3418-82) of the film formation of the redispersible particles produced leads to the desired, modifying action. The glass transition temperature can e.g. be measured by DSC methods or determined theoretically by calculations. In the present invention, the glass transition temperatures are calculated according to the Fox trial and error method (T. G. Fox, Bull. Am. Phy. Soc. (ser II) 1, 123 (1956) and Ullmann's Enzyclopädie der Technischen Chemie, vol. 19, 4th edition, Verlag Chemie, Weinheim, 1980, pp 17/18). Thus, for the glass transition temperature applies:

$$\frac{1}{Tg} = \frac{w_A}{Tg_A} + \frac{w_B}{Tg_B} + \ldots \frac{w_n}{Tg_n}$$

in which $$W_A + W_B + W_C \ldots = 1$$

and $W_A$, $W_B$, . . . represent the mass fractions of the monomers a, b and $T_{gA}$, $T_{gB}$, . . . the glass transition temperatures of the corresponding copolymers. The glass transition temperatures of certain homopolymerizates of the aforementioned monomers are known and are e.g. listed in Ullmann's Encyclopedia of Industrial Chemistry, VCH, Weinheim, vol. A21 (1992), p 169.

In certain cases it can be advantageous to choose a film-forming temperature of the (co)polymerizate above 10° C.

The nonionic monomers (a) of the present invention are understood to mean monomers which, on introduction into neutral water (pH=7) at 25° C. and 1 Atm, are unable to form an ionic charge. The inventive, nonionic monomer with the glass transition temperature above 30° C. is preferably chosen from the group consisting of styrene, styrene derivatives, such as alpha-methyl styrene, o-, m- and p-methyl styrene, o-, m- and p-ethyl styrene, o,p-dimethyl styrene, o,p-diethyl styrene, isopropyl styrene, o-methyl-p-isopropyl styrene, o,p-chloro styrene, p-bromo styrene, o,p-dichloro styrene, o,p-dibromo styrene, vinyl toluene, ethylene, vinyl acetate, vinyl chloride, vinylidene chloride, vinyl propionate, vinyl-n-butyrate, vinyl laurate, vinyl pivalate and vinyl stearate, as well as the commercially available monomers VEOVA® 9 to 11 (VEOVA X is a trade name of Shell and stands for vinyl esters of carboxylic acids, also known as VERSATIC® X-acids), (meth)acrylamide, ($C_1$–$C_{20}$ alkyl esters of (meth)acrylic acid, ($C_1$–$C_{20}$-alkenyl esters of (meth)acrylic acid with alkanols generally having 1 to 12, preferably 1 to 8 and in particularly preferred manner 1 to 4 C-atoms, such as acrylic and methacrylic acid methyl, ethyl, n-butyl, isobutyl, t-butyl and 2-ethyl hexyl esters, nitriles, alpha, beta-monoethylenically unsaturated carboxylic acids, such as acrylonitrile, as well as $C_4$–$C_8$-conjugate dienes, such as 1,3-butadiene and isoprene. It is also possible to use monomers having two vinyl groups or also two vinylidene groups or two alkylene groups, such as diesters of dihydric alcohols with alpha, beta-monoethylenically unsaturated monocarboxylic acids. It is obvious to the expert that styrene derivatives cover any random substituted styrene compounds, including e.g. styrene compounds modified by alkyl sulphonyl and carboxyl groups. Styrene and also styrene derivatives are preferred in the present invention. The quantity of nonionic monomer used in the process of the invention is, as stated hereinbefore, about 10 to 70 wt. %, based on the total weight of ethylenically unsaturated (co)monomers. Preference is given to the setting of a range of about 20 to 50, particularly about 30 to 40 wt. %, based on the total weight of ethylenically unsaturated (co)monomers.

Suitable hydrophilic, ethylenically unsaturated monomers (b) contain at least one acid functionality and are chosen from the group consisting of acrylic acid, methacrylic acid, acryloxypropionic acid, (meth)acryloxypropionic acid, acryloxyacetic acid, methacryloxyacetic acid, crotonic acid, itaconic acid, aconitic acid, maleic acid, maleic anhydride, fumaric acid, monomethyl maleate, monomethyl itaconate, monomethyl fumarate and mixtures thereof. Of these acrylic and methacrylic acid are preferred according to the invention. The hydrophilic monomer quantity should be in a range of about 5 to 30 wt. %, based on the total weight of the ethylenically unsaturated (co)monomers. Preferably, for about 1 part by weight of hydrophilic monomer having at least one acid functionality, there are about 70 parts by weight of the total (co)monomers.

The remaining conditions which must be respected when carrying out a semi-continuous emulsion polymerization and consequently also in the inventive process are known to the expert. In a semicontinuous emulsion polymerization, the monomers are continuously added to the reaction vessel. As opposed to this, during a continuous emulsion polymerization, the addition both of monomers, surfactants and initiators takes place continuously to the reaction vessel. The inventive variant of a semicontinuous emulsion polymerization has the advantage that latices with a high solids content can be prepared. Through the addition of monomers, on the one hand the mass of material present in the system is increased and on the other the concentration of other reagents can be reduced. The performance of the polymerization using the normal monomer feed procedure also makes it possible to control the viscosity of the dispersion, inter alia through the dosing time of the monomers.

Polymerization is preferably performed between about 50 and 100° C., particularly between about 60 and 90° C. The temperature can e.g. be dependent on the initiator system used. In certain cases the starting temperature is preferably about 70° C. The heat evolution due to the exothermic reaction during polymerization can be utilized in order to set the reaction temperature between 80 and 90° C. and optionally cooling may be necessary in order not to exceed the indicated temperature range. However, all the quantity of heat produced can be dissipated, so as to maintain the starting temperature of about 70° C. throughout the reaction or even drop below it. In individual cases, it is even possible to work in an autoclave, which offers the possibility of carrying out polymerization at above 100° C.

In conventional manner radical initiators are used for performing the polymerization. The radical initiators used in the invention are either water-soluble or water-insoluble, i.e. they are then monomer-soluble. Suitable water-soluble initiators are sodium, potassium and ammonium peroxodisulphate, hydrogen peroxide and water-soluble azo compounds such as 2,2'-azobis(2-amidinopropane dihydrochloride). Suitable monomer-soluble initiators are organic hydroperoxides, such as tert-butyl hydroperoxide, pinane hydroperoxide, p-menthane hydroperoxide, cumene hydroperoxide and diisopropyl phenyl hydroperoxide, organic peroxides, such as dibenzoyl peroxide, dilauryl peroxide and diacetyl peroxide, together with monomer-soluble azo compounds, such as azoisobutyronitrile. It is also possible to use mixtures of initiators. Particular preference is given to 2,2'-azobis(2-amidinopropane dihydrochloride).

In place of a radical initiator, it is also possible to use an initiator system, which comprises a radical initiator of the aforementioned type and a water-soluble reducing agent. The water-soluble reducing agents act as activators for the initiators. Suitable reducing agents are ascorbic acid, sodium, potassium and ammonium sulphite, bisulphite and metabisulphite, sodium formaldehyde sulphoxylate, tartaric acid, citric acid and glucose. They can be used in combination with a heavy metal salt. The reducing agents are generally used in a quantity of 0.01 to 2 wt. %, based on the total (co)monomers. They are generally dosed in during polymerization. The radical initiator is formed during polymerization, which can e.g. take place by the thermal decomposition of the aforementioned initiator, but also by the reaction of the initiator with an aqueous reducing agent. The initiators or initiator combination are generally used in a quantity of 0.01 to 2 wt. %, based on the total (co) monomers.

Standard additives can be concomitantly used as a function of the application conditions. Examples are thickeners, pigments, flameproofmg materials, crosslinkers, fillers, reinforcing agents, film formation aids, antioxidants, fungicides, foam inhibitors, plasticizers, preservatives, wetting agents, rheology modifying aids, vulcanizing agents, resins, adhesion aids, antiblocking agents, etc., which can be added in conventional quantities.

In conventional manner, it is also possible to use known chain transfer agents, such as e.g. alkylmercaptans, such as sec-butyl mercaptan or n-dodecyl mercaptan, bromoform and carbon tetrachloride in a quantity of about 0.01 to 5 wt. %. It is also possible to use a suitable swelling agent, which is permeable to the hydrophobic polymers of the outer phase (shell), in order to bring about a swelling of the polymer particles. Suitable swelling agents include bases of all types.

The planned control of the characteristics profile of the substrates to be modified, i.e. the improved action by the added particles, is more effective in proportion to the fineness of the particles, i.e. it is particularly advantageous of the dispersed polymerizate particles have a particularly small diameter. As a result of the process control according to the invention, it is possible to produce in planned manner substantially monodisperse latex particles with corresponding particle diameters. In this context "monodisperse" means that the average particle diameter varies by about ±10%. The average diameter of the latex particles is in a range of about 30 to 1000 and in particular about 50 to 600 nm.

The invention also relates to aqueous dispersions of latex particles having a heterogeneous morphology, obtainable by the above described process. According to a preferred embodiment of the invention the dispersion can comprise an aqueous dispersion 1 with one kind of latex particles and a further aqueous dispersion 2 with other latex particles. The weight ratio of dispersion 1 to dispersion 2 is preferably in the range of about 5:95 to 95:5, especially about 10:90 to 90:10, particularly about 20:80 to 80:20. Dispersion 2 can comprise an aqueous dispersion of homopolymers or copolymers selected from the group consisting of the monomers vinyl acetate, ethylene, vinyl versatate, acrylate, methacrylate, styrene and/or butadiene. This is only an exemplary listing and as a matter of course those skilled in the art know further monomers which can be used. By adding a further dispersion the properties of the dispersion can be optimized accordingly.

The invention also relates to latex particles having a heterogeneous morphology, which are obtainable from the aqueous dispersion by corresponding removal of the water. The latex particles obtainable according to the invention have a heterogeneous morphology, where there are hydrophilic areas substantially in an inner phase (core) and hydrophobic areas substantially in the outer phase (shell). The polymers of the hydrophilic areas are covered by the polymers of the hydrophobic areas and the polymers of the hydrophilic areas are preferably alkali-soluble. Known morphologies of latex particles are thematically represented in simplified form in FIG. 1. These are e.g. a core-shell structure (FIG. 1a), an inverse core-shell structure (FIG. 1c), a raspberry-like structure (FIG. 1b), a structure with the formation of so-called domains (FIG. 1d), a half-moon-shaped structure (FIG. 1e) or a sandwich-like structure (FIG. 1f). With the process according to the invention it is possible to prepare latex particles with a heterogeneous morphology similar to FIGS. 1b, 1c and 1d, it obviously being possible to also obtain mixed forms of said morphologies.

The latex particles can be prepared in a substantially monodisperse form according to the process of the invention, i.e. the particle diameters are in a narrow size range. In order to demonstrate this, FIG. 2 is a photograph of an inventively prepared charge of monodisperse latex particles obtained with a scanning electron microscope. Latex particles with an average particle diameter of about 70 nm are shown. FIG. 2 shows the aforementioned raspberry-like structure (cf. also FIG. 1b) of the inventive latex particles.

By adding a base, the polymer in the inner phase can be dissolved by an at least partial neutralization and can therefore completely diffuse out of the outer phase. As bases are suitable so-called swelling agents, for which the hydrophobic polymer of the outer phase is permeable, in order to bring about a swelling of the polymers. Suitable swelling agents include bases, such as ammonia, ammonium hydrochloride and volatile, lower aliphatic amines, such as morpholine, trimethyl amine and triethyl amine. It is also possible to use potassium hydroxide, lithium hydroxide, zinc ammonium complexes, copper ammonium complexes, silver ammonium complexes, strontium hydroxide, barium hydroxide, etc.

Thus, the outer phase (shell) fulfils the function of a protective shield, which both in aqueous dispersion and in powder form protects the reactive groups of the polymers of the inner phase (core), particularly the carboxyl groups against immediate reaction. This permits in planned manner a delayed release of the polymer of the inner phase in controlled portions by the addition of one of the aforementioned bases. As a result of the delayed release, it is possible to avoid an immediate sequestration, such as e.g. of the carboxyl group with metal ions in the cement, or other undesired blockings via electrostatic interaction of the reactive groups. The prevention of a direct reaction of the reactants is advantageous, if a longer processing or working time is required and it is necessary to avoid an excessively fast complete reaction of the components in the form of setting, curing, etc. This inventive effect is also not impaired by the very high concentrations of the reactive groups of the polymer of the inner phase, which can be attributed to the homogeneous distribution of the reactive groups of the polymer of the inner phase obtained according to the invention.

The invention also relates to latex particles having a heterogeneous morphology in the form of a redispersible powder, obtainable from the aforementioned aqueous dispersion by corresponding removal of the water. The removal of the water, i.e. drying, of the dispersions is in particular carried out with spray or freeze drying. A particularly favourable process for drying the aqueous dispersions is spray drying, in which the aqueous dispersion is sprayed in a warm air flow and dewatered. Preferably, the drying air and the sprayed, aqueous dispersion travel in parallel flow through the drier. The redispersible powder can be used as a pulverulent finished mixture, which only has to be stirred with water. As a function of the desired use, the powder can be redispersed in water in a more or less concentrated form.

In a preferred manner a further powder can be admixed to the powder according to the invention which results in an optimization of the properties. Thus, a powder 1 of one kind of latex particles is mixed with the further powder 2 of other latex particles. Preferably, the weight ratio of powder 1 to powder 2 is in a range of about 5:95 to 95:5, particularly about 10:90 to 90:10, especially about 20:80 to 80:20. Powder 2 can comprise homopolymers and/or copolymers selected from the following monomers vinyl acetate, ethylene, vinyl versatate, acrylate, methacrylate, styrene and/or butadiene. In the scope of the invention the monomers used herein are not limited to the above listing.

The latex particles with heterogeneous morphology in the form of an aqueous dispersion or a redispersible powder according to the invention can be used in many different ways, e.g. in composite and coating mortars, cement dyes and plastics, plastics-containing, cement-bound systems, particularly in mortar, and plastics-bound, cement-free binders, particularly in cement-free mortars, gypsum mortars, primers, plasters, carpet, wood, powder and floor adhesives, as well as in wallpaper paste, disperse powdered dyestuffs and glass fibre composite systems. These inventive, aqueous dispersions and the latex particles obtainable therefrom by drying, particularly in the form of redispersible powders, are e.g. suitable for modifying cement building adhesives, for improving processability and for increasing water resistance. Apart from a preferred use in tile adhesives, use in cement-containing products of a general nature is possible. Based on the cement, the polymerizate is generally added in a quantity of about 3 to 30 wt. %, advantageously about 7 to 20 wt. %. An inventively modified mortar has excellent processing characteristics, as are required by the processor. Typically, such modified mortars contain about 50 to 85 parts by weight sand (arithmetic mean of the particle size diameter in the range about 0.1 to 0.3 mm), about 15 to 40 parts by weight cement and the inventive polymerizate in the polymer/cement weight ratio about 0.03 to 0.30. It is obviously possible to add, as required, various additives such as cellulose, fibres, etc.

The latex particles, particularly in the form of a redispersible powder, are also suitable as a filling material for columns in chromatographic separation processes, such as gas chromatography or high pressure liquid chromatography (HPLC) or can be used as calibrating material for particle size measuring instruments, e.g. in SEM, TEM and light diffusion equipment, because, as a result of the production process, the particles have a largely identical diameter, i.e. are homogeneous or monodisperse.

Inventive latex particles, particularly in the form of redispersible powder, can also be used as carriers for the delayed release of active substances of all types. The substances can be supplied either by polymerizing in the (co)polymerizate particles or adding during the redispersion of the particles. The substance obtained can then be released in delayed manner, which can e.g. take place by adding or introducing into a substance-dissolving medium. The substances used can be employed in the agricultural sector, e.g. as fungicides, herbicides, phytohormones, insecticides, nematicides, rodenticides and acaricides. In the food sector, vitamins, mineral substances and the like are suitable as active substances, which can be delivered in delayed form by means of the redispersible powder. It is also possible to use the inventive latex particles, particularly in redispersible powder form, in the pharmaceutical sector, as inert carrier materials for receiving medicaments to be subsequently released.

The invention leads to numerous advantages. The use of protective colloids or surfactants during emulsion polymerization can be reduced, which generally permits the prevention of coagulation during polymerization and during spray drying. There is no need for spraying and drying aids. There is no need for antiblocking agents. It has surprisingly been found that the storage stability both of the dispersion and also the latex particles, particularly in the form of a redispersible powder, is significantly improved and in addition the water resistance of the latex particles is better. If use is made in the inner phase of acid-functional monomers, which can be released by alkali, there is an improvement to the processing characteristics, e.g. the adhesion and binding capacity in cement. These characteristics are also maintained in the case of high concentrations of reactive groups of the polymer in the inner phase. Thus, the present, invention makes it possible to encapsulate hydrophilic monomer units in high concentration, so that e.g. a premature reaction or crosslinking with metal ions, such as calcium, aluminium and magnesium in hydraulic or metal ionic binding systems is prevented. The delayed reaction between e.g. the carboxyl groups and the metal ions during application, compared with slightly functionalized latex polymers, can lead to surprising binding and coating characteristics. In addition, apart from the processability, the shear stability is also excellent, because the hydrophobic, inert, outer phase (shell) protects the hydrophilic polymers of the inner phase (core). Compared with other, heterogeneous latex structures, the product performance and also handling are significantly improved, so that the products according to the invention are superior to prior art products. By mixing the aqueous dispersion according to the present invention with a further dispersion or mixing the powder of the present invention with a further powder the desired properties can be optimized and an adaption to the intended application can be obtained. The latex particles according to the invention, particularly in the form of a redispersible powder, are also particularly advantageous as inert carrier materials for numerous substances, e.g. from the agricultural, food and pharmaceutical sectors. These active substances can consequently be easily dosed and used in a more planned manner as a result of the delayed release. The specific latex morphology according to the invention consequently leads to surprising characteristics of the latex particles.

EXAMPLES

Hereinafter the invention is described in detail by means of examples, which are not intended to restrict the inventive teaching. Within the scope of the disclosure, further embodiments are apparent to the expert.

The following abbreviations are used in the examples:

| MMA | Methyl methacrylate |
|---|---|
| BA | Butyl acrylate |
| MAPTAC | N-[3-(trimethyl ammonium)-propyl]-methacrylamide chloride |

-continued

| DMAPMA | N-[3-(dimethyamino)-propyl]-methacrylamide |
|---|---|
| DMAPMA-epi | N,N-[3-(chloro-2-hydroxypropyl)-3-dimethyl ammonium propyl]methacrylamide chloride |
| AA | Acrylic acid |
| St | Styrene |
| PVOH | Polyvinyl alcohol |
| GMA | Glycidyl methacrylate |
| TRITON ® | Rohm & Haas mark for a range of nonionic surfactants and VEOVA ® 10 Vinylesters of Versatic 10 ® (VEOVA ® X is a Shell mark and stands for vinylesters of carboxylic acids, which are also known as Versatic ® X-acids). |

Example 1

To a 2 liter glass reactor, equipped with a stirrer and a thermostat, were successively added 5.0 g of Triton® X-405, 0.8 g of sodium lauryl sulphate and 470 g of deionized water. Beforehand were provided 12.0 g of the subsequently used monomer mixture (in this example consisting of styrene, acrylic acid, methacrylic acid and butyl acrylate). This was followed by scavenging with nitrogen and heating to 80° C., accompanied by stirring. One minute latter 1.0 g of 2,2'-azobis-(2-amidinopropane)-dihydrochloride (Wako Chemicals GmbH, hereinafter called V-50) was added in a single portion. On reaching this temperature, simultaneously 15.0 g of a 50% aqueous solution of MAPTAC (N-[3-(trimethyl ammonium)-propyl]-methacrylamide chloride) were dosed in during 30 minutes together with 60.0 g of deionized water. 30 minutes after the start of the above feeds, 1.7 g of V-50, dissolved in 60 g of water, were dosed in during three and a half hours. It was ensured that during the entire time the temperature was kept at 80 to 85° C. 30 minutes after the start of polymerization, a monomer mixture of 200 g of styrene, 10 g of acrylic acid, 100 g of methacrylic acid and 250 g of butyl acrylate was dosed in over a three hour period. When all the feeds had ended, cooling took place to 35° C. The solids represented 50%, the viscosity was 1431 mPas and the pH-value 2.7. The average latex particle diameter was 70 nm ±5 nm and the latex particles had a so-called raspberry-like structure (occluded morphology).

Example 2

Example 1 was repeated, but polymerization took place with methyl methacrylate as the comonomer instead of styrene. Due to the different interfacial tensions and hydrophilicity, the same latex morphology as in example 1 was not obtained with MMA. The solids represented 50%, the viscosity was 163 mPas and the pH-value 2.8. The particle size was between 65 and 75 mn and there was a homogeneous latex structure.

Example 3

Example 1 was repeated, but only sodium lauryl sulphate (SLS) was used as the stabilizer for emulsion polymerization. To a 2 liter glass reactor, equipped with a stirrer and a thermostat, were successively added 10.0 g of sodium lauryl sulphate and 540 g of deionized water. Beforehand were provided 4.8 g of the subsequently used monomer mixture (in this example consisting of styrene, acrylic acid, methacrylic acid, 2-ethyl hexyl acrylates and butyl acrylate). Subsequently scavenging took place with nitrogen and heating to 80° C., accompanied by stirring. One minute later 0.2 g of ammonium persulphate (hereinafter called APS) was added in one portion. Immediately following the start of the above addition, 1.5 g of APS, dissolved in 60 g of water, and a monomer mixture of 300 g of styrene, 10 g of acrylic acid, 120 g of methacrylic acid, 120 g of butyl acrylate and 40 g of 2-ethyl hexyl acrylate was dosed in during a three and a half hour period. It was ensured that throughout this time the temperature was kept at 80 to 85° C. When all the feeds were ended, cooling took place to 35° C. The solids represented 50%, the viscosity was 7120 mPas and the pH-value 2.3.

Hereinafter are explained certain application examples showing the improved characteristics of the dispersions in cement-containing products.

Example 4

For the use testing of the polymer dispersions of examples 1 and 2, the following mortar mass composition was used as a basis:
60.0 g of quartz sand according to DIN 1164, part 7, particle group 0.1 to 0.3 mm,
35.0 g of Portland cement CEM 52.5,
24.0 g of water,
0.4 g of cellulose (MH2000xp, Herkules) and
5.0 g (co)polymerizate latex particles.

The adhesive strength, wet storage and water resistance were determined. Adhesive strength evaluation was based on the draft for European standard CEN/prEN 1348 of October 1993. The parameters were measured as follows:
Adhesive strength:
A 50 mm×50 mm clay tile (EN 176) after an insertion time, was loaded within 5 minutes of application with 20 N for 30 sec. Adhesive strength testing took place after 28 days.
Wet storage:
A 50 mm×50 mm clay tile (EN 176), after an insertion time, was loaded within 5 minutes after application with 20 N for 30 sec. The wet storage testing took place after 7 days standard climate and 20 days under water.
Water resistance:
If the adhesive strength after wet storage is divided by the standard storage (dry storage), the resulting percentage corresponds to the water resistance. The smaller the figure the worse the water resistance.

The following table shows the results obtained:

TABLE

| Copolymerizate Example No. | Processability | Adhesion Standard (N/mm$^2$) | Adhesion Wet storage (N/mm$^2$) | Wet/ standard (%) |
|---|---|---|---|---|
| 1 | very good | 0.87 | 1.11 | 127.6 |
| 2 | very poor | 0.95 | 0.66 | 69.5 |
| PVOH-stabilized St/BA | very good | 1.07 | 0.67 | 62.6 |

It is extraordinary that the (co)polymers with a high carboxyl group content according to the invention have such a good processability. In example 2 (comparison example), where the inventive morphology is not present, the processability is very poor, because normally immediately an undesired sequestration occurs. The heterogeneous latex morphology according to the invention makes it possible to delay the release of the carboxyl groups. As a result of the delayed release, it is e.g. possible to prevent an immediate sequestration with metal ions in the cement. The controlled release of reactive groups permits a later sequestration and consequently increases the adhesive strength on mineral substrates, particularly after wet storage.

What is claimed is:
1. A process for preparing an aqueous dispersion of latex particles having a heterogeneous morphology by a semicontinuous emulsion polymerization comprising:
   forming a surfactant, or protective colloid; and
   forming an emulsion polymer by a semicontinuous process from a monomer mixture, using said surfactant, or protective colloid,
   wherein said monomer mixture comprises:
      10 to 70 percent by weight of at least one nonionic, ethylenically unsaturated monomer whose homopolymer has a Tg above 30° C.; and
      5 to 30 percent by weight of at least one hydrophillic, ethylenically unsaturated monomer, wherein the nonionic, ethylenically unsaturated monomer and the at least one hydrophillic, ethylenically unsaturated monomer are simultaneously added to the dispersion,
   and wherein the latex particles have good storage stability and water resistance and have raspberry and/or domain structures.
2. The process of claim 1 further comprising forming said emulsion polymer in the presence of an in situ seed polymer.
3. The process of claim 2 wherein said seed polymer comprises from 0.01 to 25 percent by weight of said emulsion polymer.
4. The process of claim 1 wherein said protective colloid is a (co)polymer stabilizer having cationic functionality.
5. The process of claim 4 wherein said cationic functionality comprises a quaternary ammonium group.
6. The process of claim 4 wherein said cationic (co) polymer stabilizer is formed in an aqueous medium in which the monomer mixture is subsequently polymerized.
7. The process of claim 1 wherein said monomer mixture further comprises an anionic functional monomer.
8. The process of claim 4 wherein said monomer mixture comprises at least one monomer having at least one protonated reactive group, which is capable of becoming deprotonated by raising the pH-value of the aqueous dispersion.
9. The process of claim 1 wherein the homopolymer of said nonionic, ethylenically unsaturated monomer has a Tg of from 50° C. to 110° C.
10. The process of claim 1 wherein said nonionic, ethylenically unsaturated monomer is styrene or a styrene derivative.
11. The process of claim 1 wherein said hydrophillic, ethylenically unsaturated monomer comprises at least one acid functional monomer.
12. The process of claim 11 wherein said acid functional monomer is an acrylic or methacrylic acid.
13. The process of claim 11 wherein the ratio of said acid functional monomer to the other monomers in the emulsion polymer is about 1:70.
14. The process of claim 1 wherein said latex particles are monodisperse and have an average diameter of from 30 to 1000 nm.
15. An aqueous dispersion of latex particles formed by the process of claim 1.
16. The aqueous dispersion of claim 15 comprising a mixture of the latex particles formed by the process of claim 1 with at least one dispersion containing other latex particles.
17. Latex particles formed by the process of claim 1 which have been dried by the removal of water from the aqueous dispersion.
18. The latex particles of claim 17 wherein said particles have a heterogeneous morphology having a hydrophilic inner phase and a hydrophobic outer phase.
19. The latex particles of claim 17 wherein said hydrophilic phase is alkali-soluble.
20. The latex particles of claim 17 wherein said particles are redispersible in an aqueous medium.
21. A method of using the latex particles of claim 17 comprising the step of placing the particles in composite and coating mortars, cement dyes, adhesives, plastics cement-bound system, cement-free binders, wallpaper pastes and glass fiber composite systems.

* * * * *